(12) United States Patent
Hils

(10) Patent No.: US 6,710,595 B1
(45) Date of Patent: Mar. 23, 2004

(54) DISCRETIZED MAGNETIC FIELD IN EDDY CURRENT PROBE

(76) Inventor: Christopher Hils, 4204 272$^{nd}$ Ave. NE., Redmond, WA (US) 98053

( * ) Notice: Subject to any disclaimer, the term of this patent is extended or adjusted under 35 U.S.C. 154(b) by 0 days.

(21) Appl. No.: 10/228,764

(22) Filed: Aug. 27, 2002

(51) Int. Cl.$^7$ .......................... G01N 27/72; G01N 27/82
(52) U.S. Cl. ........................ 324/242; 324/241; 324/220
(58) Field of Search ................................. 324/219, 220, 324/221, 226, 228, 236, 237, 238, 241, 242, 243, 262

(56) References Cited

U.S. PATENT DOCUMENTS

| | | | | |
|---|---|---|---|---|
| 5,659,248 A | * | 8/1997 | Hedengren et al. | 324/242 |
| 5,864,232 A | * | 1/1999 | Laursen | 324/220 |
| 6,023,986 A | * | 2/2000 | Smith et al. | 73/866.5 |
| 6,232,773 B1 | * | 5/2001 | Jacobs et al. | 324/220 |
| 6,288,538 B1 | * | 9/2001 | Aruga et al. | 324/232 |
| 6,339,327 B1 | * | 1/2002 | Potiquet et al. | 324/220 |
| 6,344,739 B1 | * | 2/2002 | Hardy et al. | 324/220 |

* cited by examiner

*Primary Examiner*—Jay Patidar
(74) *Attorney, Agent, or Firm*—David L. Tingey

(57) ABSTRACT

The directed field array comprises a cylindrical solenoid 10 and a base 20 located transverse the solenoid axis 11. An array of mutually spaced apart posts 24 extends from the base 20 such that the magnetic field 22 passes through the base 20 and into the array of posts 24, dividing and focusing the magnetic field into discretized magnetic field divisions 22' through the several posts. In a first configuration, the base 20 is disposed transverse the end of the coil center or core 12 with the array of posts 24 extending from the base 20 away from the solenoid 10 longitudinally with the solenoid axis 11. In an alternative configuration, at least one base 20" locates at a solenoid end 30 transverse the solenoid axis 11 with an array of posts 24" extending radially from the base 20, equally spaced apart circumferentially about the base. Multiple bases are typically aligned with their posts staggered. In a further enhancement of this embodiment, two solenoids 10" are aligned end to end with the one or more bases 20" between them. The cylindrical solenoids 10" are electrically driven to generate opposing magnetic fields both directed into the base and radially out the posts for a combined magnetic field greater than the magnetic field from either solenoid alone.

22 Claims, 6 Drawing Sheets

DISCRETIZED MAGNETIC FIELD IN EDDY CURRENT PROBE

BACKGROUND

1. Field of the Invention

This invention relates to eddy current probes, and more specifically to a probe with at least one solenoid coil generating a electromagnetic field, the field focused and spatially discretized through an array of posts through which a magnetic field passes.

2. Prior Art

It is known in the art that variations in conductivity and permeability of a material indicate the presence of structural defects such as cracks and corrosion. These variations can be measured by propagating a primary magnetic field into the material to create eddy currents. The eddy currents generated in the material then generate a return magnetic field that is detected by the probe coil. Defects in such materials that decrease the conductivity and disrupt the eddy currents cause the magnitude of the return magnet field to decrease.

When the material is without flaws, the two magnetic fields are largely out of phase and the fields partially cancel, which reduces the coil voltage. Therefore, the probe coil voltage increases to indicate that the test coil is adjacent a defect. Signature characteristics of the flaw appear as a small modulation of the return magnetic field carrier signal. Thus, the sensitivity of the probe and the ability to sense the signature of the flaw is directly dependent on the magnitude of the incident primary magnetic field. It is therefore advantageous to have a magnetic field maximum field strength.

SUMMARY OF THE INVENTION

An eddy current probe comprises at least one solenoid generating a magnetic field. The field passes through a directed field array of mutually spaced apart high permeability posts that discretizes the magnetic field into separate magnetic fields with increased field strength. The field passes from the solenoid center, typically including a core, into an array base and through the posts and not through air space separating the posts. The magnetic field is thereby focused into the respective posts resulting in increased field strength. Fields of increased strength then emerge from post ends in a pattern of discretized and regularly-separated magnetic fields. Such a pattern of closely arranged but separated magnetic fields are particularly advantageous in eddy current signal processing. The discretized magnetic fields generate eddy currents at a well-defined higher spatial resolution much improved over the resolution that an unimproved same-sized solenoid would otherwise produce. A pick-up coil at or near each post end is positioned to detect small features within the material in coordination with the same resolution directed by the several posts. Thus a single large core can be used to generate a plurality of discrete magnetic fields with fine resolution that are disposed to excite eddy currents in a proximate test material. The eddy currents generate return magnetic fields that are detected at the point of excitation by the pick-up coil at the post end. Use of the single large core as the field-generating source is more cost-effective in probe production and more reliable in performance than a plurality of much smaller solenoid coils that would have to substitute for the several posts for similar functional effect.

A first embodiment of the eddy current probe directed field array includes a planar base installed transverse a solenoid coil at the end of a coil center or core. The array of posts extends from the base away from the solenoid longitudinally with the solenoid axis. The magnetic field generated by the solenoid along the solenoid axis then propagates through the posts in enhanced and discretized magnetic fields divided from the original solenoid magnetic field. Such a configuration is amenable for testing of flat or near flat surfaces, such as an airplane wing, by passing the array of posts over the flat surface with the posts perpendicular to the surface.

A second embodiment of the directed field array is an array of posts extending from the base radially, spaced apart circumferentially about the base. The magnetic field is then directed through the base and through the array of posts radially from the solenoid axis. Such a configuration is amenable for testing an inner surface of a tubular material by passing the solenoid through the material, the post ends extending to a position proximate the tube inner surface.

An enhancement of this second embodiment is to configure two such cylindrical solenoids axially end to end. The base may lie transversely across and between solenoid ends or the base may be annular around a single core common to coils of both solenoids, lying intermediate the solenoid core, typically central. Opposing magnetic fields combine and pass through the annular base, or ring, radially from the solenoid. (For these purposes, "opposing magnetic fields" or similar term means fields of like polarity that mutually repel.) The combined electromagnetic fields of the two opposing solenoids are thus focused through and out of the ends of the posts of the central base.

End bases may be located at distal ends of the end-to-end solenoids transverse the solenoid axis. The end bases may also include radial posts disposed outward about base circumferences. Magnetic fields effectively emerge from the posts of the central base with a large radial component and return to the posts of the end bases. This configuration of a pair of solenoids bounded by radial rings produces a combined magnetic field greater than the field from either solenoid alone. The enhanced and discretized magnetic field is thus better able to penetrate a test material proximate the post ends and is especially suitable as a probe to excite eddy currents for measuring and locating defects from within a tube as the probe is advanced through the tube.

The combined magnetic field emanating from the flat ends of the posts divide into symmetric fields about the ring each adapted to penetrate into a tubular test material proximate the rings. The combined magnetic field comprises a lead field symmetric with a following field that is concentrated radially outward from the center ring. With two symmetric and identical fields, as the dual solenoid configuration moves axially in a tube, one of the magnetic fields, as a lead field, is disposed to first encounter an anomaly in the tube before the other, or following magnetic field encounters it. Return magnetic fields generated by eddy currents in the tube that are induced by the lead and following magnetic fields are thus amenable to differencing that removes a carrier component common in the two return magnetic fields largely leaving only the component due to the material anomaly that is modulated on the carrier component.

DETAILED DESCRIPTION OF THE PREFERRED EMBODIMENT

Figure 1:
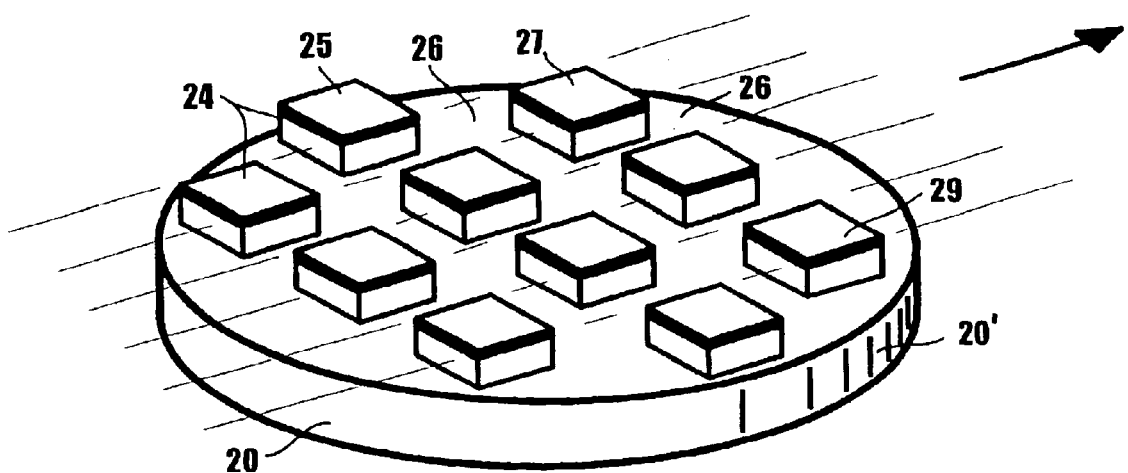
FIG. 1 is a perspective view of the directed field array in a first configuration with a staggered orthogonal pattern of posts depending from a base FIG. 2 front plan view of the directed field array of FIG. 1.
Figure 2:
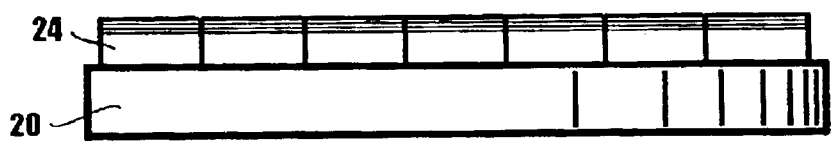

The directed field array of the present invention comprises a magnetic field source, typically a cylindrical solenoid 10 with a drive coil 9 and an axis 11, and preferably including a core 12 through the solenoid, and a base 20 located transverse the solenoid axis 11, or generally transverse the magnetic field 22. An array of mutually spaced apart posts 24 extends from the base 20, the base and the posts being constructed of high permeability material. The base 20 and posts 24 are adapted such that the magnetic field 22 passes through the base 20 and into the array of posts 24, dividing and focusing the magnetic field into discretized magnetic field divisions 22' through the several posts.

Figure 3:
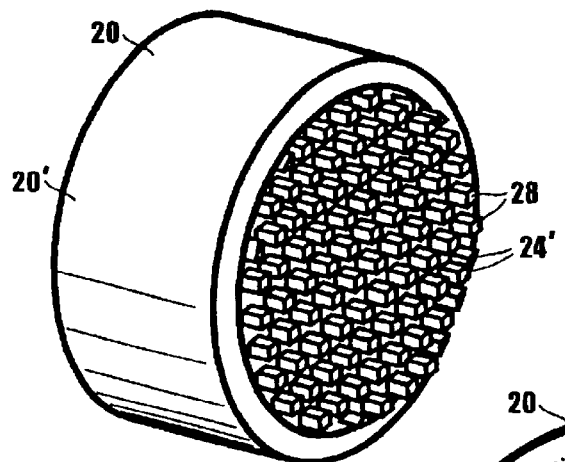
FIG. 3 is a perspective view of the directed field array in an unstaggered configuration.
Figure 4:
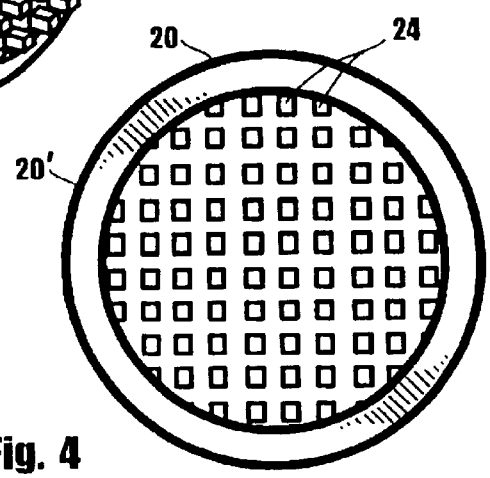
FIG. 4 is a top view of the directed field array of FIG. 3
Figure 5:
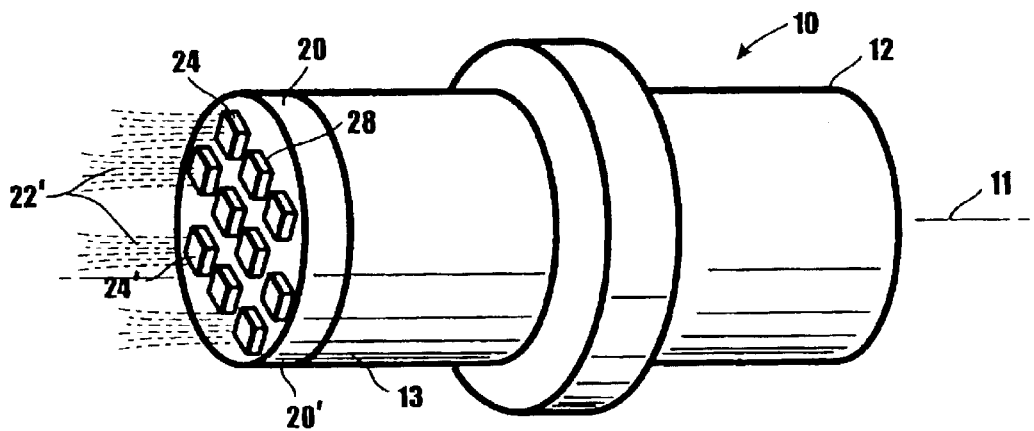
FIG. 5 is a perspective view of the directed field array of FIG. 1 shown on the end of and transverse a solenoid.

In a first configuration, the base 20 is planar and disposed transverse the end of the coil center or core 12 with the array of posts 24 extending from the base 20 away from the solenoid 10 longitudinally with the solenoid axis 11. FIG. 3 and FIG. 4 show the posts in a normal orthogonal pattern; FIG. 1 shows the array with the posts 24 in a staggered orthogonal pattern. That is, in a staggered array a second row 25 of posts 24 is aligned with interstitial spaces 26 between a first row 27 of posts 24 so in combination the posts map continuous coverage as the array translates generally perpendicular to the rows 25 and 27 so at least one post 24 passes over any given portion of a surface and collectively the posts 24 pass over the entire test material inner surface.

As incorporated into an eddy current probe designed to measure a flat surface, a planar base 20' is located on a solenoid core end 13 with orthogonally disposed posts 24' directed away from the solenoid core 12, adapted such that ends 28 of the array of posts pass in close proximity to the material flat surface perpendicular to the surface.

Figure 7:
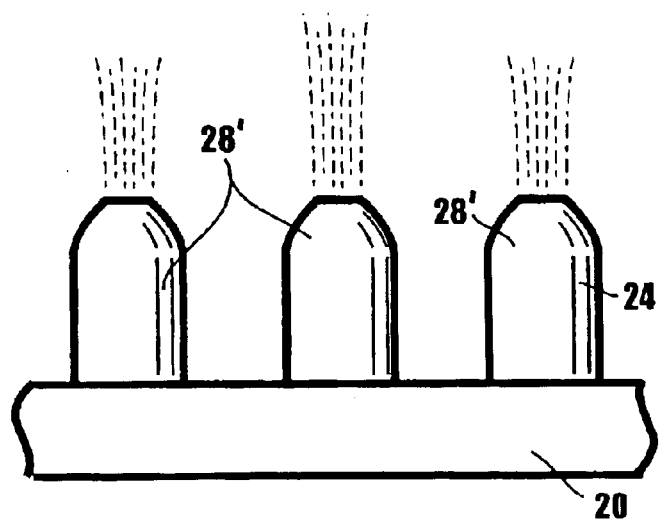
FIG. 7 is a side view of a row of posts with posts each curving to a reduced end to further focus discretized magnetic fields emanating from post ends of reduced size.

Each post typically terminates in a flat end 29 matching a surface of a flat material to be tested, but not necessarily so. For example, as shown in FIG. 7, post ends 28' may be highly curved or pointed to further focus the magnetic field emerging from the post, useful for even higher field strength or resolution.

Figure 6:
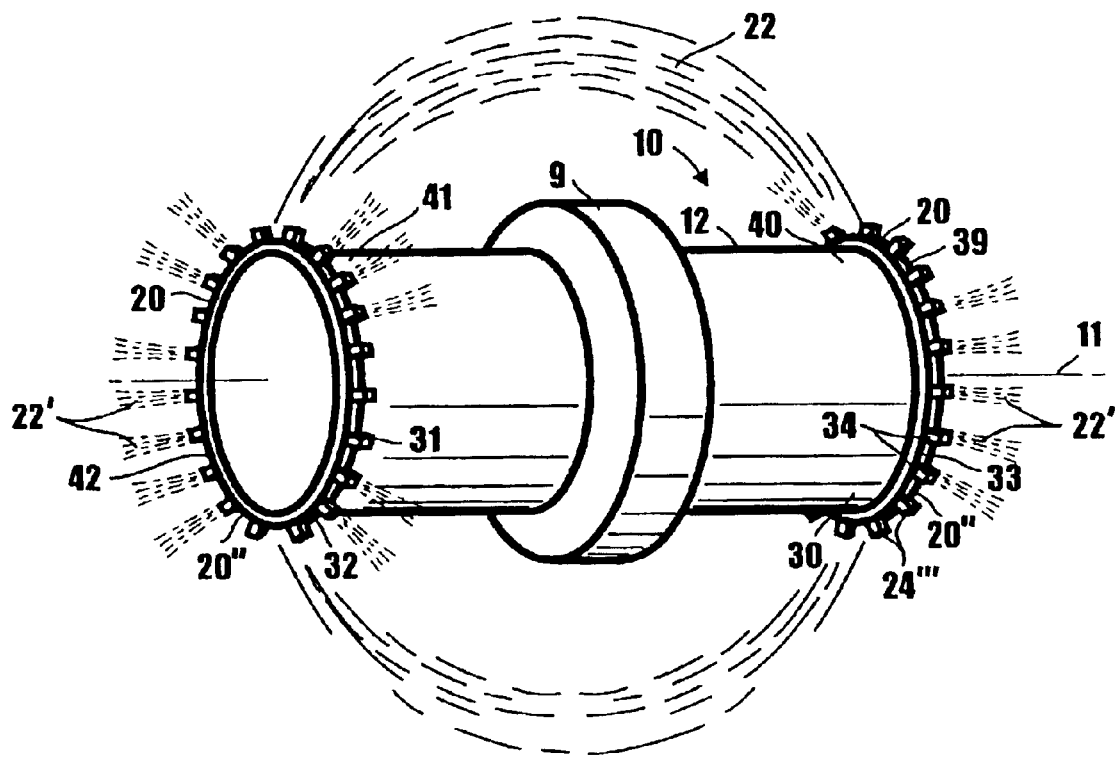
FIG. 6 is a perspective view of a second embodiment of the directed field array showing a cylindrical base with an array of radially extending posts equally spaced circumferentially about the ring shown on each end of a solenoid in staggered relation.
Figure 8:
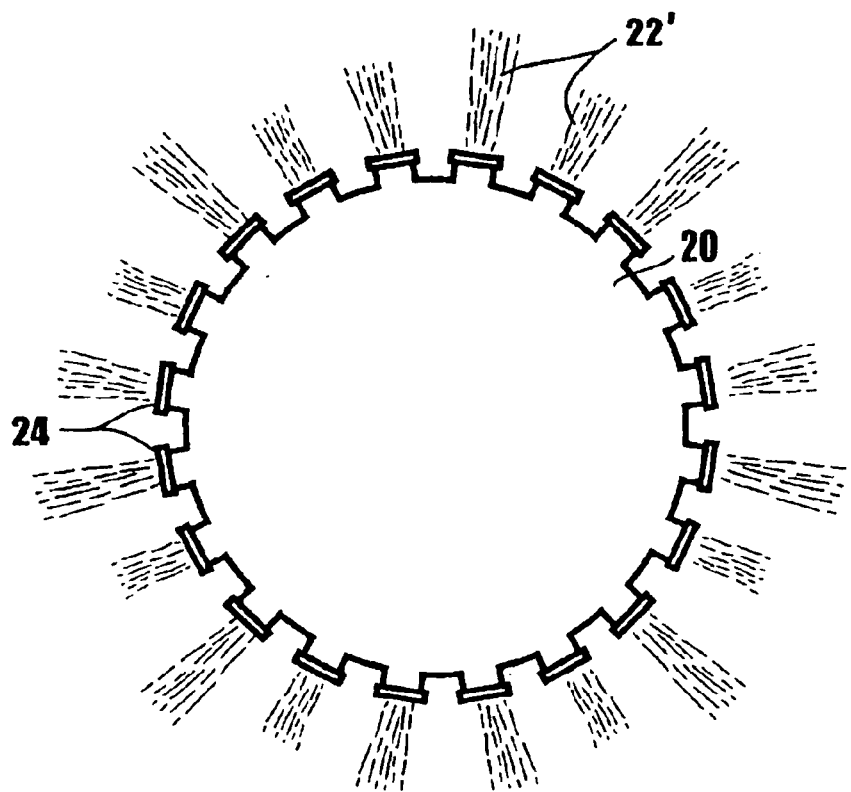
FIG. 8 is a front view of the directed field array of FIG. 6, shown with discretized magnetic fields emanating from the several radial posts.
Figure 9:
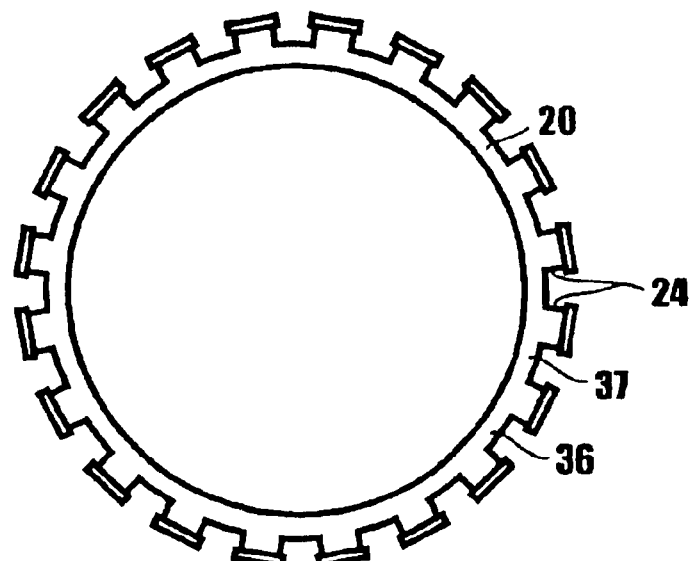
FIG. 9 is a front view of the directed field array of FIG. 6, shown with an annular base.

In an alternative or second configuration shown in FIG. 6, at least one base 20" locates at a solenoid end 30 transverse the solenoid axis 11 with an array of posts 24" extending radially from the base 20", equally spaced apart circumferentially about the base. Multiple bases are typically aligned with their posts staggered, a following post 31 of a second base 32 tracking interstitial areas 33 between posts 34 of a first base 35, so in combination the bases map continuous coverage circumferentially around the solenoid 10 so at least one post 24" passes over any given portion of an inner surface of a tubular test material and collectively the posts pass over the entire test material inner surface. In a further enhancement of this embodiment, two solenoids 10" are aligned end to end with the one or more bases 20" between them. The cylindrical solenoids 10" are electrically driven to generate opposing magnetic fields both directed into the base and radially out the posts as shown in FIG. 8. This configuration effectively produces a combined magnetic field within the base 20" greater than the magnetic field from either solenoid alone. In practice, the dual solenoid embodiment comprises two coils 34 would cylindrically around a solenoid core 12.

A base 35 central on the core 12 is typically annular, a ring 36 comprising an annular base 37 in a plane perpendicular to the core axis 11. A plurality of central posts 24" extends radially from the annular base 37 in the plane, typically terminating in respective flat ends 29. The central posts 24" are spaced apart equidistantly around the annular base 37 focusing the magnetic fields through the posts, again increasing the field strength not only due to the combination of fields from the two opposing coils but also from directing the combined fields through the plurality of spaced-apart posts. The circumferential spacing between the posts is dictated by a preferred spatial resolution of the measurement. The posts are of such length and separation as to promote the propagation of the magnetic field through and out of the post at a flat end into a test material proximate the post end 28.

An end ring 39 similar to the central ring 36 is typically located on distal ends 40 and 41 of the core 12 through which the magnetic field returns. The end rings 39 also comprise an annular base 42 in respective parallel planes perpendicular to the core axis 11. Likewise, a plurality of end posts 24''' may extend radially from the base 42 with the respective posts spaced equidistantly apart around the base. Typically, the posts 24''' of the central ring 36 are staggered in longitudinal alignment from posts 24''' of the end rings 39 so the posts collectively pass over the entire inner surface of a tubular test material. Two of said end rings 39 may be driven by a single solenoid 10 with the end rings 39 respectively located at solenoid opposite ends 40 and 41.

In another configuration, a ring 39 with radial posts 24" also may be located central on a solenoid core 12 between two solenoid coils 36. The coils are electrically driven such that magnetic fields resulting from alternating electric current in the coils are opposing between them at the rings 39.

Figure 10:
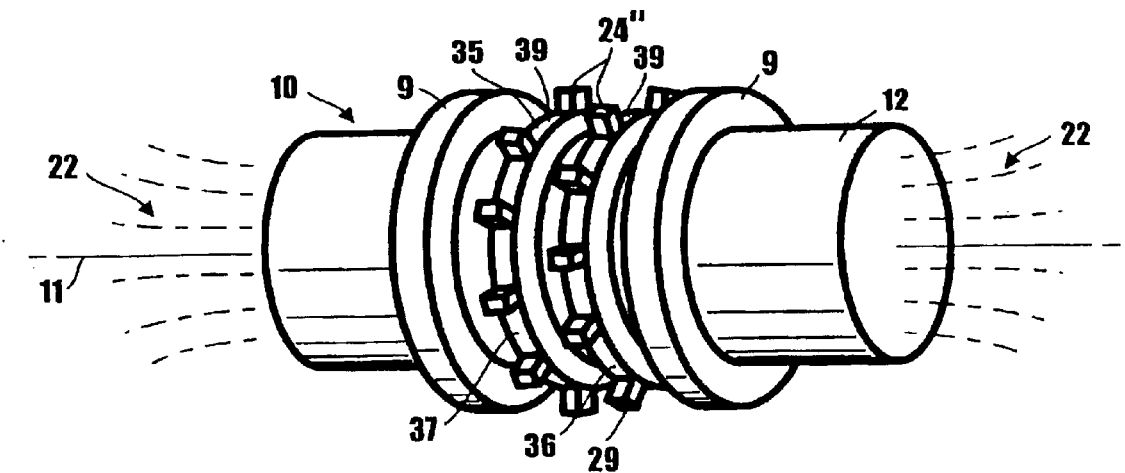
FIG. 10 is a perspective view of two directed field arrays as in FIG. 6 shown between two solenoids intended to be electrically connected to produce opposing magnetic fields.

That is, like magnetic poles from the two solenoid coils meet at the rings, resulting in their magnetic fields combining and emerging from the solenoid core at the rings with a magnetic field strength greater than either alone. As shown in shown in FIG. 10, equivalently two rings 39 with radial posts 24" also may be located central on a solenoid core 12 between two solenoid coils 36, again typically in staggered relation to collectively cover the entire test material. In this configuration of two solenoid coils.

Figure 11:
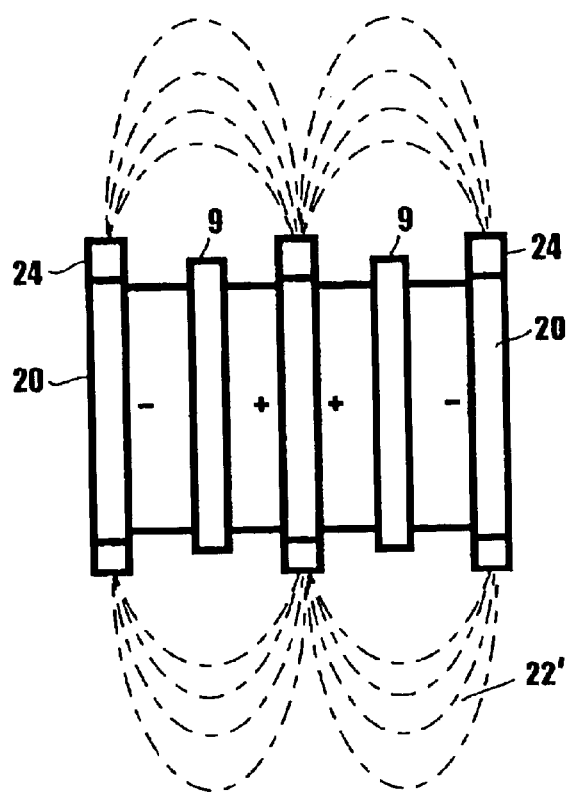
FIG. 11 is an artist's rendition of representative magnetic fields of the directed field array of FIG. 8, shown sectionally through a central plane dividing the solenoids. The magnetic fields shown are for a pair of posts for simplicity of illustration. Actually, the field pattern repeats around the dual solenoid configuration.

As shown in FIG. 11, the combined magnetic field emanating from the flat ends of the posts divide into symmetric fields about the ring each adapted to penetrate into a tubular test material proximate the rings. With two identical fields, as the dual solenoid configuration moves axially in a tube, one of the magnetic fields, as a lead field, is disposed to first encounter an anomaly in the tube before the other, or following magnetic field encounters it. Return magnetic fields generated by eddy currents in the tube that are induced by the lead and following magnetic fields are thus amenable to differencing that removes a carrier component common in the two return magnetic fields largely leaving only the component due to the material anomaly that is modulated on the carrier component.

Figure 12:
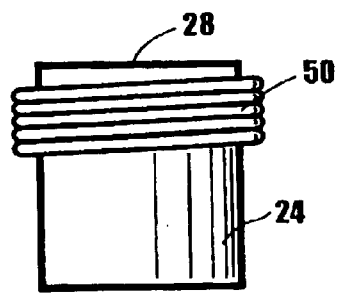
FIG. 12 shows a side view of a pick-up coil around an array post.
Figure 13:
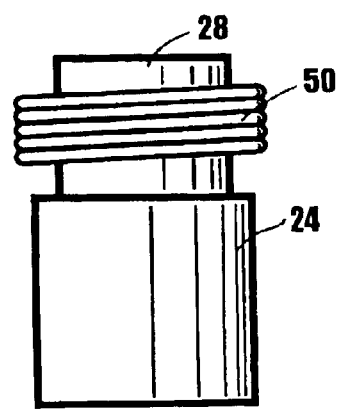
FIG. 13 shows a side view of a pick-up coil in front of, or beyond the end of a post.
Figure 14:
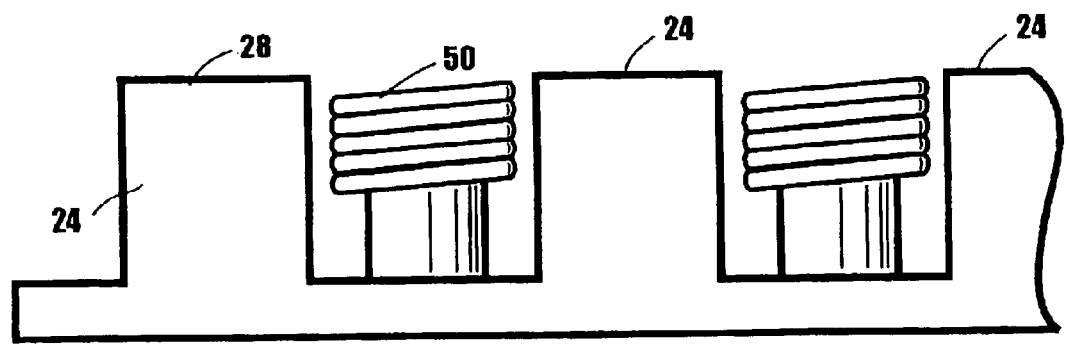
FIG. 14 shows a side view of a pick-up coil interstitially between two radial posts of the directed field array of FIG. 4.

As shown in FIG. 12, a pick-up coil 50 at or near each post end 28 is positioned to detect small features within the material in coordination with the same resolution directed by the several posts 24. Typically, a pick-up coil 50 is wound around each array post 24 coaxial with said respective posts to preserve the detection resolution enabled by the discretized magnetic fields through the posts. As shown in FIG. 13, with similar affect, the pick-coil 50 may be between the respective post 24 and the test material, separate from the post. As shown in FIG. 14, the pick-coil 50 also may be interstitially between the array posts. As used herein, "pick-up coil" should be interpreted generally to include all known transducers for sensing magnetic fields, including pick-up coils, Hall sensors, and magneto-resistive devices, suitably positioned and installed to sense a return magnetic field generated by eddy currents.

The figures illustrate representative configurations of spaced-apart posts on bases in relation to drive coils of a solenoid. These are representative only. It is recognized that many other combinations and configurations are possible and effective in delivering spatially discretized directed magnetic fields. All such combinations and configurations are deemed included in this disclosure.

Having described the invention, what is claimed is as follows:

1. An eddy current probe, comprising
   a first solenoid, with a drive coil having a longitudinal axis, generating a fluctuating magnetic field,
   a directed field array including
      a base of material having high magnetic permeability transversely intersecting the magnetic field, the magnetic field being conducted into the base,
      a plurality of mutually spaced apart posts of material having high magnetic permeability depending from the base, the magnetic field conducted from the base discretized into the posts and out of post distal ends, the plurality of posts disposed on the base such that post ends are amenable to positioning proximate a material to be tested by directing the magnetic field of the solenoid in discretized magnetic fields emerging from post ends into said test material therein inducing eddy currents in said test material,
   at least one transducer proximate at least one post end, adapted to detect a magnetic field generated from said eddy currents.

2. The eddy current probe of claim 1, wherein the plurality of posts depend perpendicularly from the base in a plurality of parallel rows, each row comprising a plurality of spaced apart posts with interstitial spaces therebetween and coverage gaps between ends of adjacent posts in a row, with posts of one or more other rows aligned with interstitial spaces of a first row in a direction of translation perpendicular to said first row such that ends of posts of said other rows map over said coverage gaps when said array of posts translates laterally in said direction of translation.

3. The eddy current probe of claim 1 in which the posts are equidistantly spaced apart in a row.

4. The eddy current probe of claim 1 wherein said ends of said posts have a curvature matching test material surfaces to which said posts may be positioned in proximity for testing of the material.

5. The eddy current probe of claim 4 wherein said ends of said posts are flat.

6. The eddy current probe of claim 1 in which one of said at least one transducer comprises a pick-up coil around a post of one of said plurality of posts near said post distal end.

7. The eddy current probe of claim 1 in which said transducer comprises a pick-up coil beyond said post ends.

8. The eddy current probe of claim 1 in which said transducer is adjacent one of said plurality of posts.

9. The eddy current probe of claim 1 in which the directed field array is on an end of the first solenoid, the base transverse the solenoid axis, the posts parallel to the solenoid axis.

10. The eddy current probe of claim 1 in which the base is cylindrical and the posts extend radially about the base circumference spaced apart equidistantly with interstitial spaces therebetween and coverage gaps between ends of adjacent posts.

11. The eddy current probe of claim 10 further comprising one or more further cylindrical bases intersecting said magnetic field also with posts spaced apart equidistantly extending radially about the base circumference wherein posts of the further cylindrical bases are aligned with interstitial spaces of the first cylindrical base in a direction of translation parallel with the solenoid axis such that ends of posts of the further cylindrical base map over said coverage gaps when the solenoid translates in said direction of translation.

12. The eddy current probe of claim 11 wherein the solenoid coil is between the first base and a further base.

13. The eddy current probe of claim 11 further comprising a second solenoid with a second drive coil aligned coaxially end to end with said first solenoid, the solenoid coils electrically driven to generate opposing magnetic fields with both fields directed into at least one base and radially out the posts of said at least one base, the at least one base between drive coils of the first and second solenoids.

14. The eddy current probe of claim 13 wherein posts of the first base and said further base are in staggered relation.

15. The eddy current probe of claim 13 further comprising two bases between drive coils of the first and second solenoids, posts of the two bases in staggered relation.

16. The eddy current probe of claim 13 further comprising a single solenoid core with the solenoid coils around the at least one core, the at least one base comprising an annular ring around the core between the solenoid coils with the posts extending radially from the ring.

17. The probe of claim 1 wherein the posts extend in the plane of the base.

18. The eddy current probe of claim 10 further comprising
   a solenoid core,
   a left base and a right base on respective left and right core ends.

19. The eddy current probe of claim 13 further comprising
a solenoid core,
a left base and a right base on respective left and right core ends.

20. The probe of claim 19 wherein the at least one base and the left and right bases each comprise
an annular base in respective parallel planes perpendicular to the core axis, and
a plurality of end posts extending radially from the annular base in the respective planes.

21. The probe of claim 20 wherein the posts of the at least one base are staggered from posts of the end bases.

22. An eddy current probe comprising
end-to-end coaxial solenoid coils divided by a coaxial annular base transverse the solenoid coils and connectable to electric current to produce opposing magnetic fields at the annular base through which base magnetic fields generated by the coils are conducted radially outward in producing lead and following separate magnet fields beyond the coils symmetric about the base and disposed such that when positioned proximate a test material the separate magnetic fields penetrate into said test material generating eddy currents in the test material that produce respective return magnetic fields modulated with signatures of material anomalies, the lead magnetic field first generating a modulated eddy current signature of an anomaly before a following magnetic field when the solenoid translates in a direction parallel the solenoid axis, a difference of said lead and following signatures resulting in a signal associated with the material anomaly.

* * * * *